US011452474B1

(12) United States Patent
Nawana et al.

(10) Patent No.: US 11,452,474 B1
(45) Date of Patent: Sep. 27, 2022

(54) DUAL LEVER DERMAL PATCH SYSTEM (71) Applicant: Neoenta LLC, Weston, MA (US)

(72) Inventors: Namai Nawana, Weston, MA (US);
Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 17/412,213

(22) Filed: Aug. 25, 2021

Related U.S. Application Data (60) Provisional application No. 63/190,700, filed on May 19, 2021, provisional application No. 63/174,956, filed on Apr. 14, 2021.

(51) Int. Cl.
A61B 5/15 (2006.01)
A61B 5/151 (2006.01)

(52) U.S. Cl.
CPC ........ *A61B 5/150969* (2013.01); *A61B 5/151* (2013.01); *A61B 5/150236* (2013.01)

(58) Field of Classification Search
CPC ............ A61M 2005/2073; A61B 2017/00367; A61B 2017/00371; A61B 2017/00398; A61B 2010/0208; A61B 5/157
See application file for complete search history.

(56) References Cited

U.S. PATENT DOCUMENTS

| 5,015,228 A | 5/1991 | Columbus et al. |
| 5,338,308 A | 8/1994 | Wilk |
| 5,441,490 A | 8/1995 | Svedman |
| 5,527,288 A | 6/1996 | Gross et al. |
| 5,848,991 A | 12/1998 | Gross et al. |
| 5,997,501 A | 12/1999 | Gross et al. |
| 6,500,150 B1 | 12/2002 | Gross et al. |
| 6,524,284 B1 | 2/2003 | Marshall |

(Continued)

FOREIGN PATENT DOCUMENTS

WO WO-2017075586 A1 * 5/2017 ............... F04B 9/14

OTHER PUBLICATIONS

U.S. Appl. No. 17/500,873, filed Oct. 13, 2021, Namal Nawana.
U.S. Appl. No. 17/521,466, filed Nov. 8, 2021, Namal Nawana.
U.S. Appl. No. 17/412,205, filed Aug. 25, 2021, Namal Nawana.

*Primary Examiner* — Patrick Fernandes
*Assistant Examiner* — Severo Antonio P Lopez
(74) *Attorney, Agent, or Firm* — Potomac Law Group, PLLC (57) ABSTRACT A system includes an applicator and a dermal patch coupled to the applicator. The applicator includes a needle configured to puncture a subject's skin to draw a physiological sample, a first actuating lever configured to move form an undeployed position to a deployed position, and a second actuating lever configured to move form an undeployed position to a deployed position. The dermal patch includes a fluid reservoir configured to store a processing fluid, a sample collection chamber configured to receive the processing fluid and the physiological sample, wherein the applicator is configured to cause the needle to puncture the subject's skin to draw the physiological sample when the first actuating lever is moved from the undeployed lever position to the deployed lever position and cause the processing fluid to release from the fluid reservoir when the second actuating lever is moved from the undeployed position to the deployed position.

19 Claims, 10 Drawing Sheets (56) References Cited

U.S. PATENT DOCUMENTS

| | | |
|---|---|---|
| 6,623,457 B1 | 9/2003 | Rosenberg |
| 6,689,118 B2 | 2/2004 | Alchas et al. |
| 6,776,776 B2 | 8/2004 | Alchas et al. |
| 6,960,193 B2 | 11/2005 | Rosenberg |
| 6,994,691 B2 | 2/2006 | Ejlersen |
| 7,651,475 B2 | 1/2010 | Angel et al. |
| 8,048,019 B2 | 11/2011 | Nisato et al. |
| 8,066,680 B2 | 11/2011 | Alchas et al. |
| 8,206,336 B2 | 6/2012 | Shantha |
| 8,246,582 B2 | 8/2012 | Angel et al. |
| 8,409,140 B2 | 4/2013 | Ejlersen et al. |
| 8,512,244 B2 | 8/2013 | Jennewine |
| 8,556,861 B2 | 10/2013 | Tsals |
| 8,622,963 B2 | 1/2014 | Iwase et al. |
| 8,696,637 B2 | 4/2014 | Ross |
| 8,715,232 B2 | 5/2014 | Yodfat et al. |
| 8,870,821 B2 | 10/2014 | Laufer |
| 9,022,973 B2 | 5/2015 | Sexton et al. |
| 9,089,677 B2 | 7/2015 | Soo et al. |
| 9,227,021 B2 | 1/2016 | Buss |
| 9,504,813 B2 | 11/2016 | Buss |
| 9,522,225 B2 | 12/2016 | Chong et al. |
| 9,566,393 B2 | 2/2017 | Iwase et al. |
| 9,724,462 B2 | 8/2017 | Rotem |
| 9,770,578 B2 | 9/2017 | Chowdhury |
| 9,968,767 B1 | 5/2018 | Hasan et al. |
| 10,888,259 B2 | 1/2021 | Jordan et al. |
| 2002/0193740 A1 | 12/2002 | Alchas et al. |
| 2004/0106904 A1 | 6/2004 | Gonnelli et al. |
| 2005/0118388 A1 | 6/2005 | Kingsford |
| 2006/0047243 A1 | 3/2006 | Rosenberg |
| 2007/0004989 A1 | 1/2007 | Dhillon |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0259176 A1 | 10/2009 | Yairi |
| 2011/0060280 A1 | 3/2011 | Caffey et al. |
| 2011/0105872 A1* | 5/2011 | Chickering, III ............ A61B 5/150297 600/365 |
| 2012/0041338 A1 | 2/2012 | Chickering, III et al. |
| 2012/0078224 A1* | 3/2012 | Lerner ............ A61M 5/3243 604/506 |
| 2012/0271123 A1* | 10/2012 | Castle ............ A61B 5/150167 600/309 |
| 2014/0194854 A1 | 7/2014 | Tsals |
| 2014/0336616 A1 | 11/2014 | Edwards |
| 2015/0073385 A1 | 3/2015 | Lyon et al. |
| 2015/0258272 A1 | 9/2015 | Sullivan et al. |
| 2016/0067468 A1 | 3/2016 | Chowdhury |
| 2016/0199581 A1 | 7/2016 | Cachemaille et al. |
| 2016/0354589 A1 | 12/2016 | Kobayashi et al. |
| 2017/0035975 A1 | 2/2017 | Myung et al. |
| 2017/0043103 A1 | 2/2017 | Wotton et al. |
| 2017/0197029 A1 | 7/2017 | Cindrich et al. |
| 2017/0224912 A1 | 8/2017 | Yodfat et al. |
| 2017/0290977 A1 | 10/2017 | Schauderna |
| 2018/0008808 A1 | 1/2018 | Chowdhury |
| 2018/0021559 A1 | 1/2018 | Xu |
| 2018/0126058 A1 | 5/2018 | Nakka David et al. |
| 2018/0243543 A1 | 8/2018 | Baek et al. |
| 2019/0001076 A1 | 1/2019 | Solomon et al. |
| 2019/0015584 A1 | 1/2019 | Meehan et al. |
| 2019/0030260 A1 | 1/2019 | Wotton et al. |
| 2019/0209820 A1 | 7/2019 | Chickering, III et al. |
| 2019/0366067 A1 | 12/2019 | Ginggen et al. |
| 2020/0009364 A1 | 1/2020 | Amir |
| 2020/0011860 A1* | 1/2020 | Nawana ............ G01N 33/49 |
| 2020/0101219 A1 | 4/2020 | Wang et al. |
| 2021/0030975 A1 | 2/2021 | Burton et al. |

* cited by examiner

DUAL LEVER DERMAL PATCH SYSTEM

CROSS REFERENCE TO RELATED APPLICATIONS

This application claim priority to and the benefit of U.S. Application No. 63/174,956, filed on Apr. 14, 2021 and U.S. Application No. 63/190,700, filed on May 19,2021, the entire teachings of both of these applications are incorporated by reference herein.

TECHNICAL FIELD

The following relates to a dermal patch and more particularly to a dermal patch for storage of a physiological sample and/or detection of an analyte in a physiological sample.

BACKGROUND

Biomarkers are increasingly employed for diagnosis of various disease conditions as well as for assessing treatment protocols. Unfortunately, the invasive nature of drawing a blood sample from a patient can cause discomfort and may lead to less cooperation from a subject, especially children, and hence render obtaining a physiological sample that may contain a target biomarker difficult.

Some recently developed dermal patches allow for the detection target biomarkers, but typically suffer from a number of shortcomings, such as low sensitivity and/or specificity. Some dermal patches allow a user to obtain a physiological sample in order to send the obtained sample to a laboratory for further analysis that may not be able to be performed on the patch itself. Unfortunately, these dermal patches fail to provide a physiological sample preservation fluid within the dermal patch. This failure makes sample storage and preservation impractical thus rendering such at home sample collection solutions unsatisfactory.

SUMMARY

Aspects of the present disclosure address the above-referenced problems and/or others.

In one aspect, a system for collecting a physiological sample is disclosed, which includes an applicator having a needle that is configured to puncture a subject's skin to allow drawing a physiological sample from the subject as well as a first and a second actuating lever, each of which is configured to move form an undeployed position to a deployed position. The system further includes a dermal patch (herein also referred to as a dermal patch cartridge) that is configured for coupling to the applicator. The dermal patch can include a fluid reservoir configured to store a processing fluid and a sample collection chamber that is configured to receive the physiological sample. In some embodiments, the sample collection chamber is further configured to receive the processing fluid. The applicator can be configured to activate the needle so as to puncture the subject's skin to allow drawing the physiological sample when the first actuating lever is moved from its undeployed lever position to its deployed lever position and cause the processing fluid to be released from the fluid reservoir when the second actuating lever is moved from its undeployed position to the deployed position.

In some embodiments, the applicator can be removably coupled to the dermal patch. In other embodiments, the applicator and the dermal patch can form a single integral unit.

A system according to the present teachings can be employed to collect (and in some embodiments analyze the collected sample) physiological samples, such as blood and interstitial fluid.

A variety of processing fluids (typically liquids) can be stored on the dermal patch. By way of example, and without limitation, the processing fluid can be an anti-coagulant (e.g., heparin), a protease inhibitor, a preservative, or any other processing fluid suitable for preparing a physiological sample for collection and/or analysis.

In some embodiments, an adhesive layer coupled to the dermal patch can allow attaching the dermal patch to a subject's skin.

In some embodiments, the second actuating lever is in a locked state when the first actuating lever is in the undeployed position. For example, a latch can inhibit the movement of the second actuating lever so long as the first actuating lever is in the undeployed position. The actuation of the first actuating lever by moving it from its undeployed position to its deployed position can release the latch to allow actuation of the second actuating lever.

In some embodiments, the applicator can further include a vacuum chamber in which a syringe is movably positioned. The syringe can be activated by moving the first actuating lever from its undeployed position to its deployed position so as to create a vacuum in the vacuum chamber. When the applicator is coupled to the dermal patch, the vacuum chamber will be in fluid communication with one or more fluidic channels within the dermal patch such that the creation of the vacuum in the vacuum chamber will result in generating a vacuum in those channels, thereby facilitating collection of the physiological fluid and its transfer, as well as the transfer of the processing fluid, to the sample collection chamber.

In a related aspect, a system for analyzing a physiological sample is disclosed, which includes an applicator and a dermal patch, where the dermal patch is configured for attachment to a subject's skin and the applicator is configured for coupling, e.g., removable coupling, to the dermal patch for activating the dermal patch. The applicator can include a needle that is configured to puncture a subject's skin to allow drawing a physiological sample from the subject.

The applicator can further include a first and a second actuating lever, each of which is configured to move from an undeployed position to a deployed position. The dermal patch can include a fluid reservoir that is configured to store a processing fluid, which can be mixed with a drawn physiological sample to generate a processed physiological sample, and a sensor that is configured to detect a target analyte in the processed physiological sample. The applicator is further configured to cause the needle to puncture the subject's skin to allow drawing the physiological sample when the first actuating lever is moved from its undeployed lever position to its deployed lever position and to cause the processing fluid to be released from the fluid reservoir when the second actuating lever is moved from the undeployed position to the deployed position.

The sensor incorporated into the dermal patch can be configured to detect the target analyte when the target analyte is present in the processed physiological sample at a concentration level equal to or greater than a threshold amount.

A variety of processing fluids, such as those discussed herein can be employed. In some embodiments, the processing fluid can include one or more reagents needed for isothermal amplification of a target analyte.

An applicator/dermal patch system according to the present teachings can be employed to detect a variety of analytes in the drawn physiological sample. By way of example, the analyte can be a biomarker. Some examples of biomarkers that can be detected using an applicator/dermal patch system according to the present teaching can include, without limitation, troponin, brain natriuretic peptide (BnP), myelin basic protein (MBP), ubiquitin carboxyl-terminal hydrolase isoenzyme L1 (UCHL-1), neuron-specific enolase (NSE), glial fibrillary acidic protein (GFAP), S100-B, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, or HbAlC.

In other embodiments, the analyte of interest may be a pathogen, such as a bacterium and/or a virus.

A variety of sensors can be incorporated in various embodiments of a dermal patch according to the present teachings. Some examples of such a sensor can include, without limitation, an immunoassay sensor, an isothermal amplification detection system, a graphene-based sensor, an electrochemical sensor, and chemical sensor.

In some embodiments, the second actuating lever can be in a locked state when the first actuating lever is in its undeployed position. By way of example, the applicator can include a latch that is configured to lock the second actuating lever when the first actuating lever is in an undeployed position.

In some such embodiments, the actuation of the first actuating lever, e.g., via moving it from its undeployed position to its deployed position, can unlock the second actuating lever, e.g., by releasing the latch, thereby allowing the actuation of the second actuating lever.

In some embodiments, the applicator can further include a vacuum chamber in which a syringe is movably position. The syringe can be activated, via the movement of the first actuating lever from its undeployed position that is configured to create a vacuum within the dermal patch when the first actuating lever is moved from the deployed position to the undeployed position, wherein the vacuum draws the physiological sample and the released processing fluid to flow to the well.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description when taken in conjunction with the accompanying drawings in which.

DETAILED DESCRIPTION

The present disclosure generally relates to a system and method that may be utilized to collect and store a physiological sample (e.g., blood, interstitial fluid, etc.) and/or detect a target analyte in a collected physiological sample.

In some embodiments, a dermal patch system according to the present teachings can include a dermal patch and an applicator that is configured for coupling to the dermal patch. A user can actuate the applicator to cause the activation of the dermal patch so as to collect a physiological sample. The dermal patch may include a processing fluid (e.g., reagent, buffer, anticoagulant, etc.), for persevering the physiological sample and/or preparing the physiological sample for analysis. Providing a system with a dermal patch that includes a processing sample allows for the collection and preservation of a physiological sample within the dermal patch. Such a system may allow a user of the system to collect a physiological sample themselves at home and store the collected sample for further testing.

In other embodiments, a dermal patch of a dermal patch system according to the present teachings may be configured to detect one or more target analytes (e.g., a biomarker) in a physiological sample. As discussed in more detail below, in some such embodiments, the applicator can include one or more needles that can be deployed, when an actuating lever of the applicator is moved from an undeployed position to a deployed position, to puncture the skin so as to allow the collection of a physiological sample into the dermal patch. For example, the collection of the physiological sample can be facilitated using the applicator to create a vacuum in one or more fluidic channels of the dermal patch. In embodiments, subsequent to collection of at least some of the physiological sample into the dermal patch, another actuating lever of the applicator can be actuated to release at least a portion of the processing fluid on-board of the dermal patch such that the release processing fluid can mix with the drawn physiological sample. In some such embodiments, both the physiological sample and the processing fluid can be directed onto a detector incorporated in the dermal patch. By way of example, the processing fluid may be suitable for amplification of a target analyte (e.g., a primer), or otherwise preparing a physiological sample for analysis. Such embodiments of a dermal patch system according to the present teachings can provide ease of use and further allow facile collection and analysis of a physiological sample, among other advantages.

In embodiments, the use of two actuating levers, where one is used to draw a physiological sample, and the other to release a processing fluid (e.g., a buffer) for processing the physiological sample advantageously allows performing the steps of drawing a sample and processing the sample via the processing fluid in a temporal sequence. In other words, initially, a physiological sample, such as a blood sample, can be drawn, via actuation of one of the actuating levers, and transferred to a sample collection chamber (e.g., a well) or a sensor incorporated in the dermal patch. Subsequently, the processing fluid can be transferred to the sample collection chamber or the sensor to mix with the physiological sample. By way of example, in embodiments, a user can visually inspect the sample collection chamber or a chamber in which a sensor (such as a lateral flow sensor) is positioned to ensure that a sufficient amount of the physiological sample has been collected before causing the processing fluid to be released from a reservoir in which the processing fluid is stored, in a manner discussed herein.

Various terms are used herein in accordance with their ordinary meanings in the art, unless indicated otherwise. The term "about," as used herein, denotes a deviation of at most 10% relative to a numerical value. The term "substantially," as used herein, refers to a deviation, if any, of at most 10% from a complete state and/or condition. The terms "needle" and "microneedle" are used herein to broadly refer to an element that can provide a passageway, or facilitate the production of a passageway, for collecting a physiological sample, such as a blood or an interstitial fluid sample through a patient's skin, e.g., via puncturing the subject's skin. The term "transparent," as used herein, indicates that light can substantially pass through an object (e.g., a window) to allow visualization of a material disposed behind the object. For example, in some embodiments, a transparent object allows the passage of at least 70%, or at least 80%, or at least 90%, of the visible light therethrough. The term "vacuum," as used herein, refers to a pressure less than the atmospheric pressure, and more particularly to such pressure can facilitate the extraction of a physiological sample from a subject.

Figure 1A:
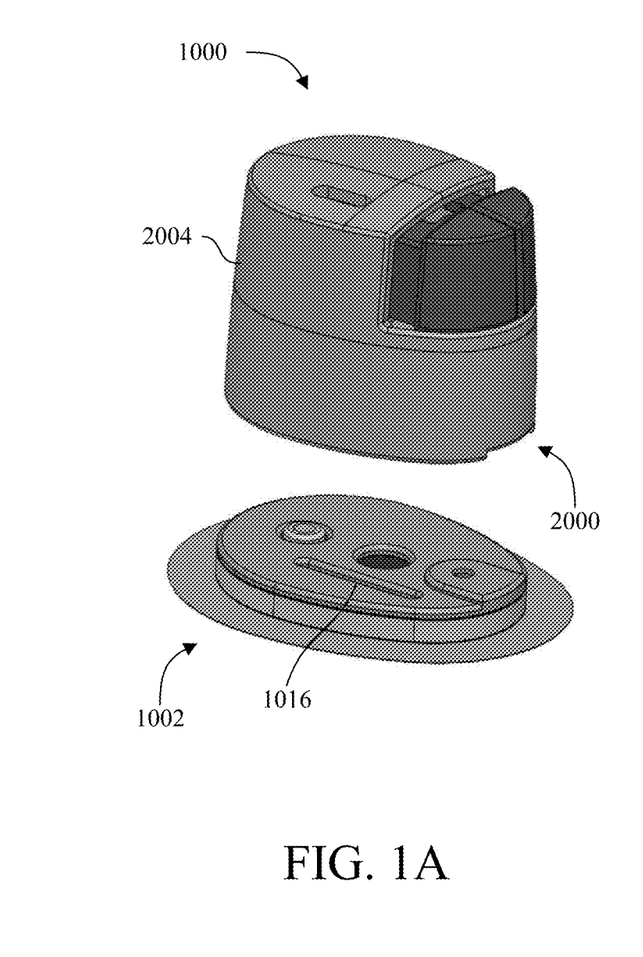
FIG. 1A depicts an applicator and a dermal patch in accordance with an exemplary embodiment.
Figure 1B:
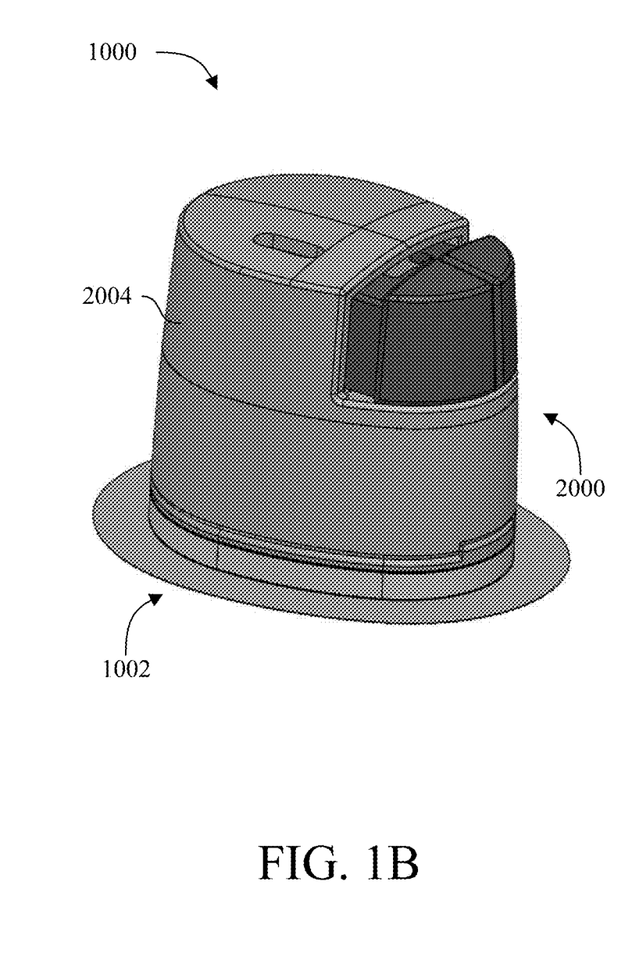
FIG. 1B depicts an applicator coupled to a dermal patch in accordance with an exemplary embodiment.

With reference to FIGS. 1A and 1B, a dermal patch system 1000 according to an embodiment includes a cartridge assembly 1002 (which is herein referred to also a dermal patch cartridge or simply a dermal patch), which can be attached to a subject's skin via an adhesive layer, as discussed in more detail below. The dermal patch system 1000 further includes an applicator 2000, which is herein also referred to as an applicator/actuator assembly, that is configured for removable coupling to the dermal patch 1002 for activating the dermal patch for drawing a physiological sample from the subject and providing analysis of the drawn physiological sample, as discussed in more detail below.

In the following discussion, the structure and operation of the dermal patch system 1000 will be described in connection with drawing a blood sample from a subject. It should be, however, understood that a dermal patch system according to the present teachings, such as the dermal patch system 1000, can be used for drawing and analyzing other types of physiological samples, such as an interstitial fluid.

FIG. 1A shows the dermal patch system 1000 in a state in which the applicator 2000 is not coupled to the dermal patch 1002 and FIG. 1B shows the dermal patch system 1000 in a state in which the applicator 2000 is coupled to the dermal patch 1002. The applicator 2000 can include a recess 2002 into which the dermal patch can be received and maintained in place.

Figure 2A:
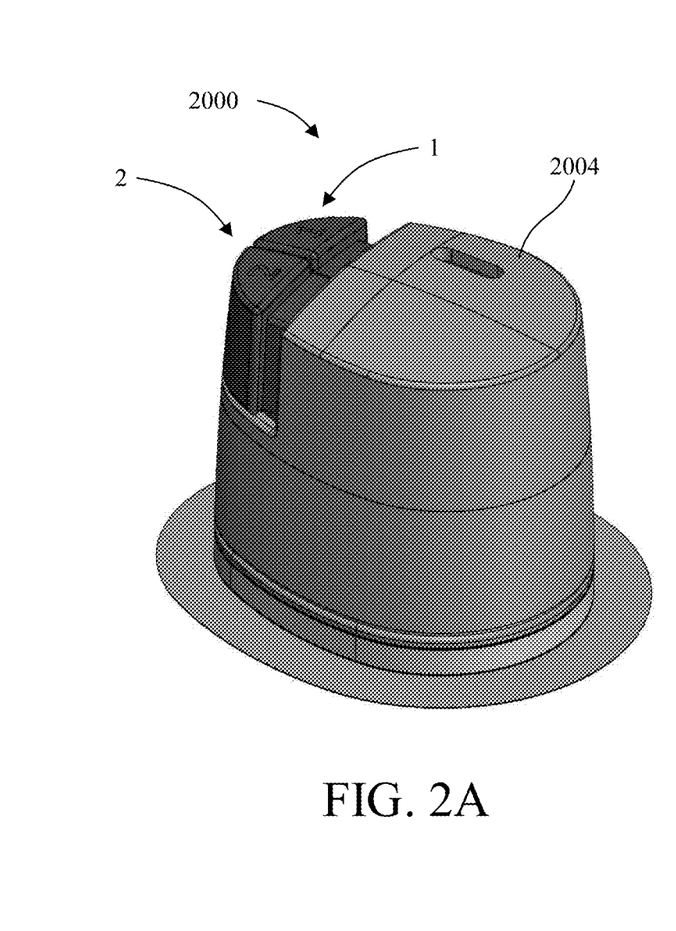
FIG. 2A depicts an applicator coupled to a dermal patch in accordance with an exemplary embodiment.
Figure 2B:
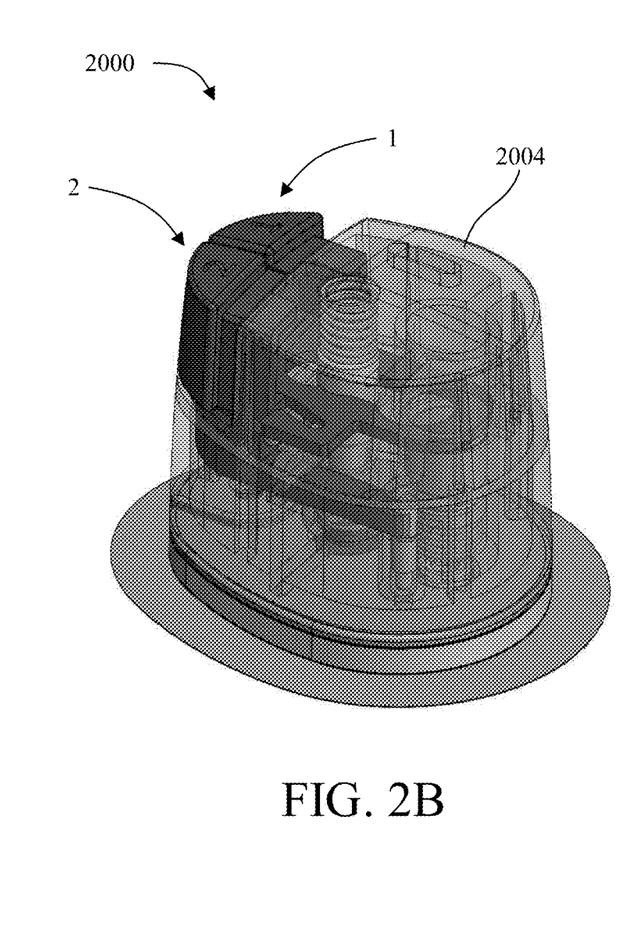
FIG. 2B depicts an applicator coupled to a dermal patch wherein a housing of the applicator is transparent in accordance with an exemplary embodiment.
Figure 3A:
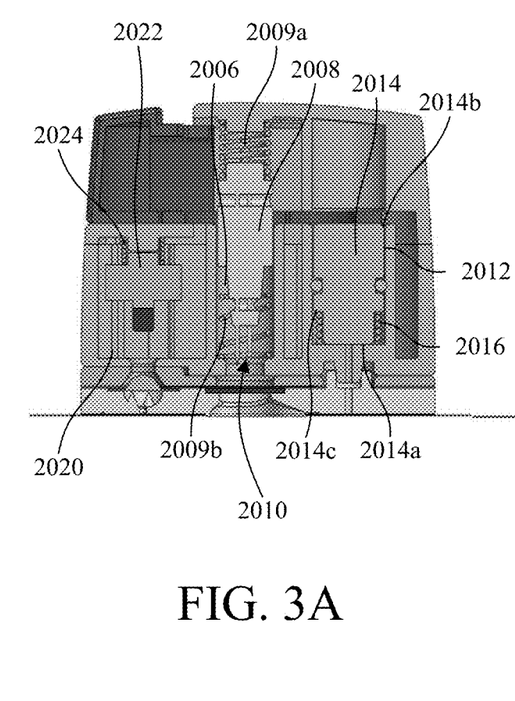
FIG. 3A is a cross sectional view of an applicator coupled to a dermal patch wherein a first actuating lever of the applicator is in an undeployed position in accordance with an exemplary embodiment.
Figure 3B:
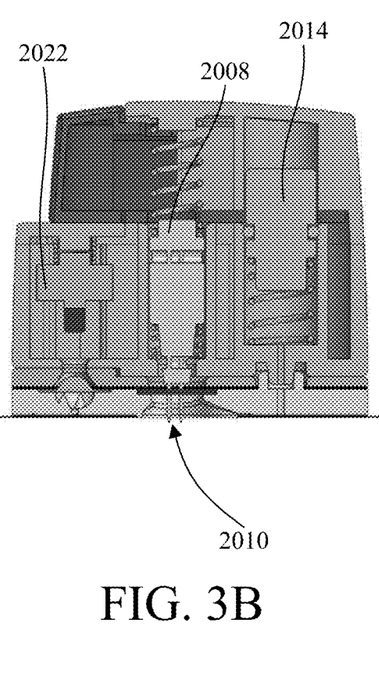
FIG. 3B is a cross sectional view of an applicator coupled to a dermal patch wherein a first actuating lever and needles of the applicator are in a deployed position in accordance with an exemplary embodiment.
Figure 3C:
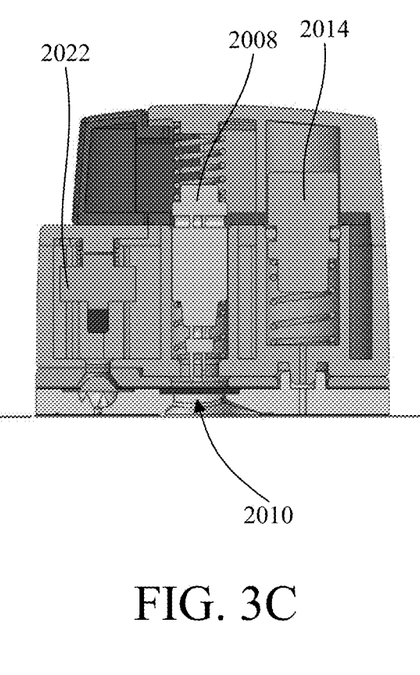
FIG. 3C is a cross sectional view of an applicator coupled to a dermal patch wherein a first actuating lever of the applicator is in a deployed position and needles of the applicator are in a retracted position in accordance with an exemplary embodiment.
Figure 3D:
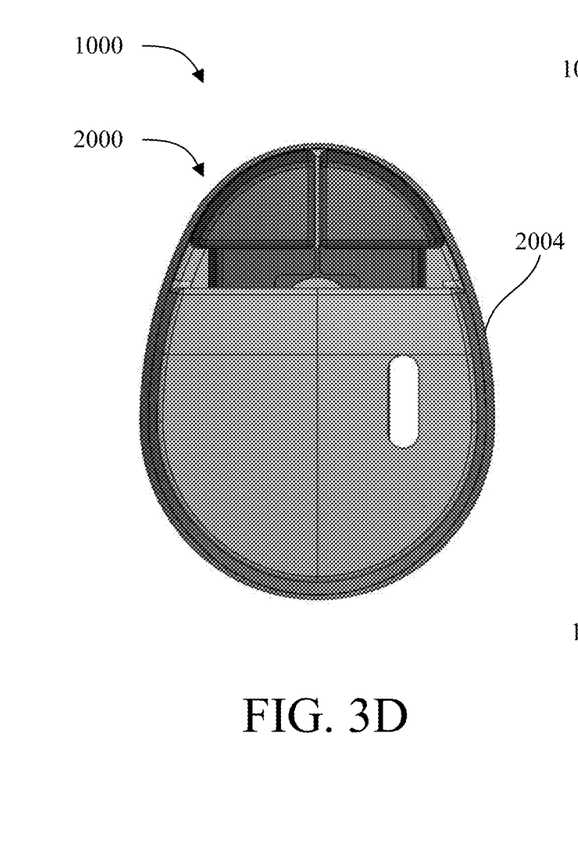
FIG. 3D is a top view of an applicator in accordance with an exemplary embodiment.
Figure 3E:
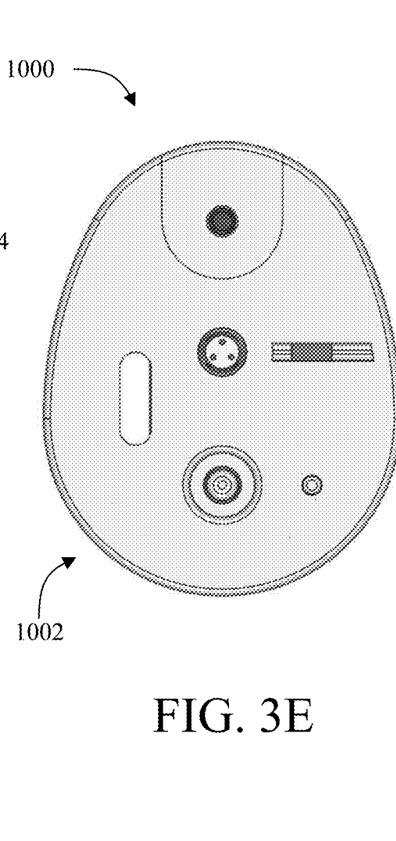
FIG. 3E is a bottom view of an applicator in accordance with an exemplary embodiment.
Figure 3F:
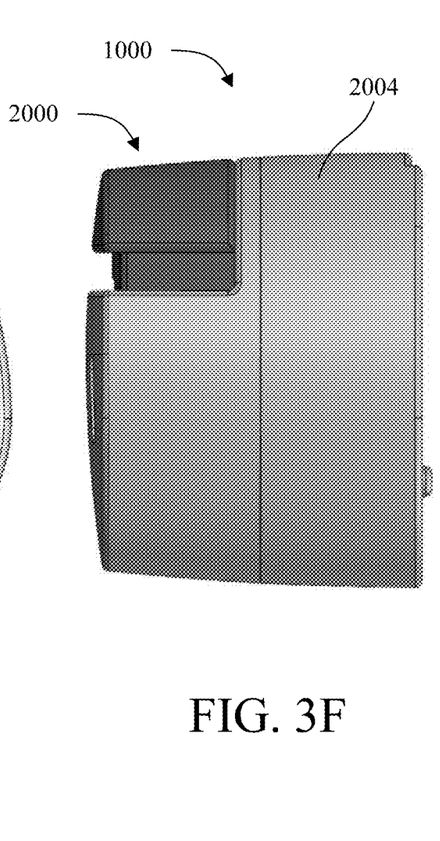
FIG. 3F is a side view of an applicator in accordance with an exemplary embodiment.

With reference to FIGS. 2A, 2B as well as FIGS. 3A, 3B, 3C, 3D, 3E and 3F, the applicator 2000 includes a housing 2004 in which various components of the applicator are disposed. With particular reference to FIGS. 3A, 3B, and 3C, in this embodiment, the applicator 2000 includes a needle chamber 2006 in which a needle mount 2008 is positioned and to which three needles 2010 are mounted (two of the needles are visible in FIGS. 3A-3C). In other embodiments, the number of needles mounted onto the needle mount 2008 can be different. By way of example and without limitation, the number of needles can be in a range of one to about 20.

In this embodiment, two biasing elements 2009a and 2009b are operably coupled, respectively, to the top and the bottom of the needle mount 2008 to facilitate its movement and consequently the movement of the needles 2010 attached thereto between a retracted position in which the needles are fully enclosed within the needle chamber 2006 (FIGS. 3A and 3C) and an extended position (FIG. 3B) in which the needles will penetrate through a septum provided in the dermal patch, as discussed in more detail below, so as to puncture the subject's skin to allow drawing a blood sample from the subject. As discussed in more detail below, the biasing elements 2009a/2009b allow activating the needle mount to puncture the subject's skin and be subsequently retracted back into the needle housing 2006.

The applicator 2000 further includes a vacuum chamber 2012 in which a syringe 2014 (herein also referred to as a plunger) is positioned. In this embodiment, the syringe 2014 extends from a proximal portion 2014a to a distal end 2014b, where the diameter of the proximal portion is less than the diameter of the distal portion, thereby forming a shoulder 2014c. In this embodiment, a biasing element 2016 is coupled to the shoulder and is in a compressed state when the syringe 2014 is in an inactive state. As discussed further below, upon activation of the syringe into an active state, the biasing element 2016 will expand, thereby moving the syringe upward and generating a vacuum within the vacuum chamber 2012. The term "vacuum" as used herein refers to any pressure below the atmospheric pressure, and particularly such a pressure that can facilitate drawing a physiological sample from the subject.

Further, the applicator 2000 includes a chamber 2020 in which a push pin 2022 (herein also referred as a processing fluid release element or simply as a fluid release element) is positioned, where the push pin 2022 is adapted to release, upon activation, a processing fluid stored in a fluid reservoir incorporated in the dermal patch 1002. In some embodiments, the processing fluid is suitable for preserving a physiological sample including, but not limited to, an anticoagulant (e.g., heparin, a protease inhibitor, etc.). In other embodiments, the processing fluid is suitable for isothermal amplification a target analyte, including but not limited to, a primer.

More specifically, in this embodiment, the push pin 2022 includes a tip 2023a that is formed of a soft material, e.g., a soft polymeric material, which upon activation can press on a membrane sealing the fluid reservoir that is incorporated in the dermal patch so as to cause the release of a processing fluid stored in the reservoir, as discussed in more detail below, e.g., by causing a puncture of at least a portion of the sealing membrane.

A biasing element in the form of a spring 10024 is coupled to the push pin 10022, which is in a relaxed state when the push pin is in an inactive state and can be compressed in a manner discussed below to activate the push pin 10022 so as to cause the release of the processing fluid from the processing fluid reservoir.

With particular reference to FIGS. 2A and 2B, in this embodiment, the applicator 2000 includes two actuating levers 1 and 2, which can be independently actuated to transition them from an undeployed position (state) to a deployed position (state). As discussed in more detail below, in this embodiment, the actuating lever 2 is locked and can be only be actuated after the actuation of the actuating lever 1.

Referring to FIGS. 4A, 4B, 4C, 4D, 4E, and 4F, the actuating lever 1 includes an actuation block 10, which is accessible to a user and an actuating arm 12 that extends from the actuation block 10. The actuating arm 12 includes two openings 12a and 12b that are connected via a channel 12c. In an undeployed position (FIG. 4A), a middle portion of the needle mount 2008 is positioned within the channel 12c, where the width of the channel 12c is such that the needle mount 2008 will be locked therein via a physical ledge, a latch and groove mechanism, an interference lock, a cantilever and groove fit, etc. Further, in an undeployed position, a distal portion 12d of the actuating arm 12 maintains the syringe 2014 in an inactive state by pressing down on the syringe, thereby compressing the biasing element 2016.

Figure 4A:
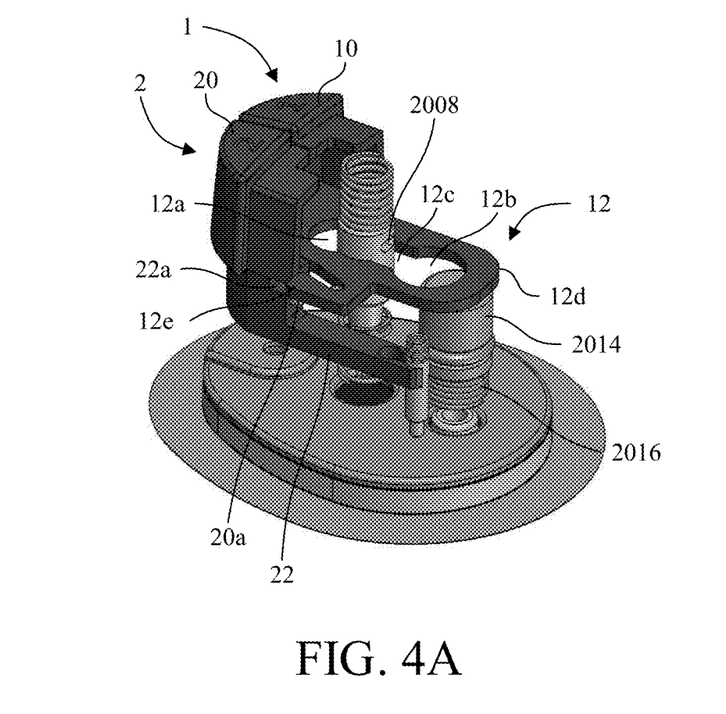
FIG. 4A depicts components of an applicator and a dermal patch wherein a first and second actuating lever of the applicator are in an undeployed position in accordance with an exemplary embodiment.

With particular reference to FIG. 4A, the actuating arm 12 further includes an appendage 12e that is configured to maintain a latch 20a (the latch 20a is better seen in FIG. 4B) that is coupled to the actuating lever 2 in a recess 22a provided in a portion of an actuating arm 22 of the actuating lever 2, so as to lock the actuating lever 2 and inhibit its actuation, when the actuating lever 1 is in an undeployed state. As discussed in more detail below, upon actuation of the actuating lever 1, the latch 20a is released to allow a user to actuate the actuating lever 2.

Figure 4B:
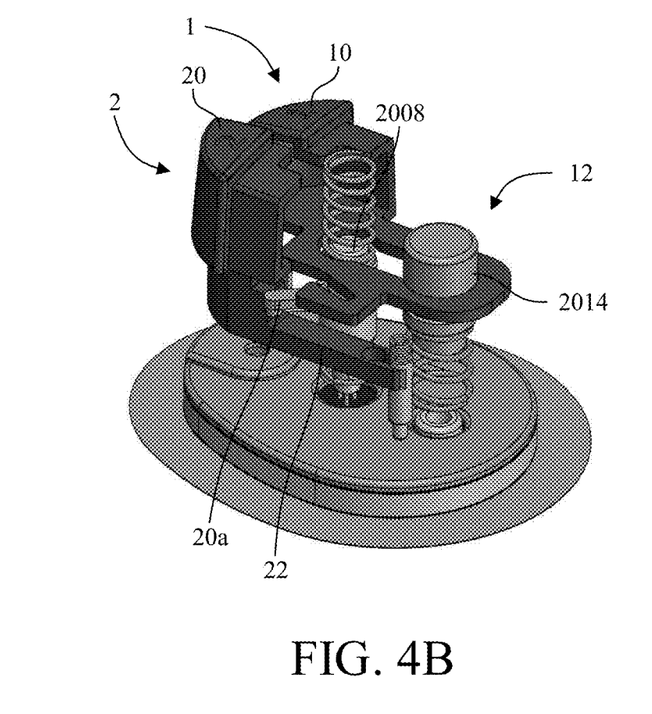
FIG. 4B depicts components of an applicator and a dermal patch wherein a first actuating lever is in a deployed position and a second actuating lever is in an undeployed position in accordance with an exemplary embodiment.
Figure 4C:
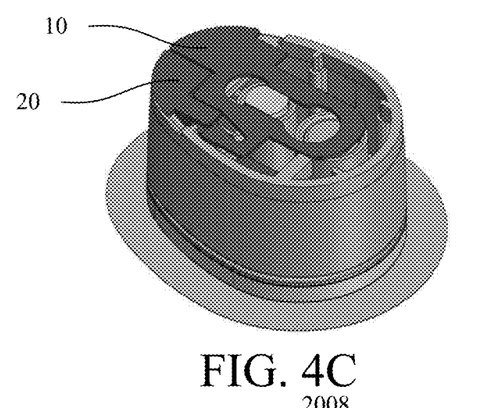
FIG. 4C depicts components of an applicator and a dermal patch wherein a first and second actuating lever of the applicator are in an undeployed position in accordance with an exemplary embodiment.
Figure 4D:
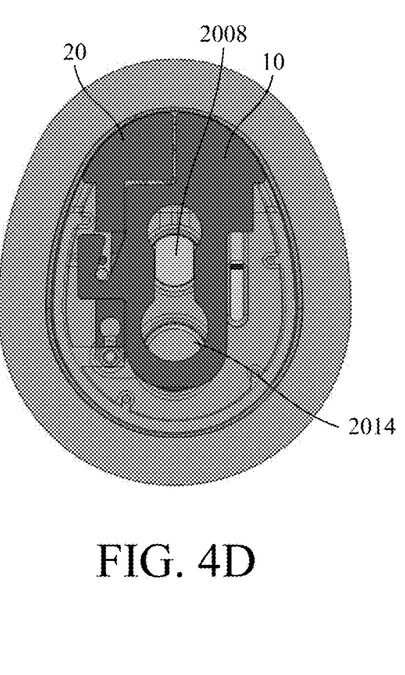
FIG. 4D is a top view of components of an applicator and a dermal patch wherein a first and second actuating lever of the applicator are in an undeployed position in accordance with an exemplary embodiment.
Figure 4E:
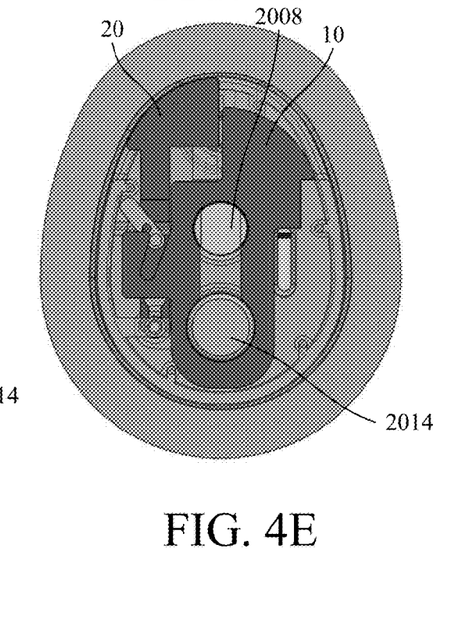
FIG. 4E is a top view of components of an applicator and a dermal patch wherein a first actuating lever is in a deployed position and a second actuating lever is in an undeployed position in accordance with an exemplary embodiment.
Figure 4F:
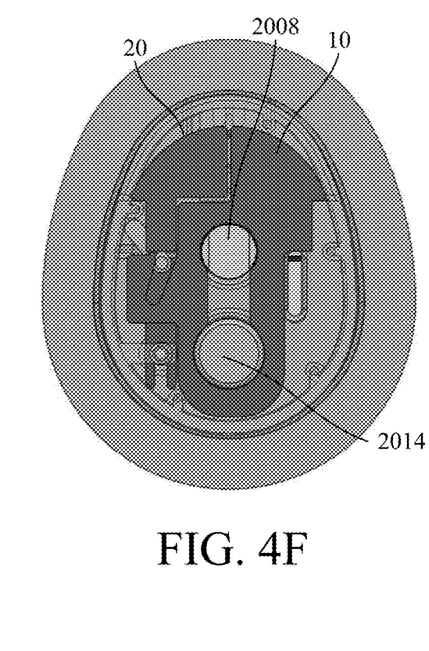
FIG. 4F is a top view of components of an applicator and a dermal patch wherein a first and second actuating lever of the applicator are in an deployed position in accordance with an exemplary embodiment.

With particular reference to FIG. 4B as well as FIGS. 3B and 3C, a user can press the actuation block 10 so as to actuate the actuating lever 1. The actuation of the lever 1 moves the actuating arm 12 such that the portion of needle mount 2008 that is locked within the channel 12c will be received in the opening 12a, thereby releasing the needle mount and allowing its movement. Upon release of the needle mount 2008, the biasing element 2009, which is in a compressed state when the actuating lever 1 in an undeployed position, expands to push the needle mount 2008 downward, thereby deploying the needles 2010 mounted thereto for puncturing a subject's skin, as discussed in more detail below. The downward movement of the needle mount causes compression of the biasing element 2009b, which is in a relaxed state when the actuating lever 1 is in an undeployed position. Once the needles puncture the skin, the expansion of the biasing element 2009a causes the needle mount 2008 and hence the needles 2010 mounted thereto to be retracted into the needle housing 2006.

Further, the actuation of the actuating lever 1 moves the distal end 12d of the actuating arm 12 so as to release the syringe 2014, thereby allowing the biasing element 2016 to expand and cause the upward motion of the syringe 2014, which generates a vacuum within the vacuum chamber 2012. As discussed in more detail below, the generation of a vacuum within the vacuum chamber 2012 facilitates drawing a blood sample through the subject's punctured skin.

Figure 5A:
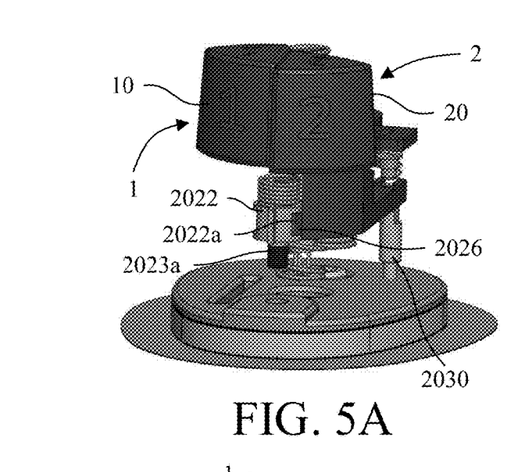
FIG. 5A depicts components of an applicator and a dermal patch in accordance with an exemplary embodiment.
Figure 5B:
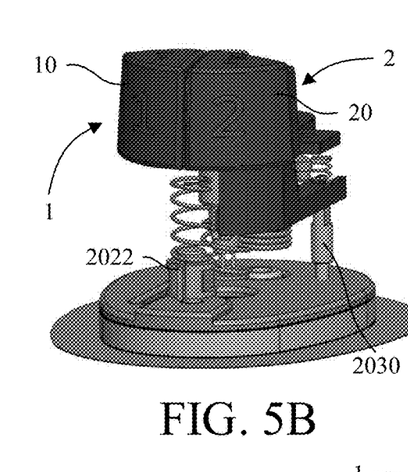
FIG. 5B further depicts components of an applicator and a dermal patch in accordance with an exemplary embodiment.
Figure 5C:
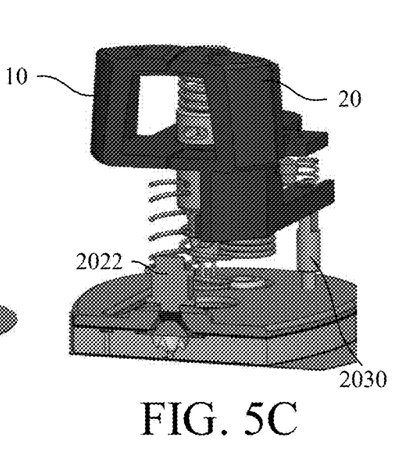
FIG. 5C further depicts components of an applicator and a dermal patch in accordance with an exemplary embodiment.

Turning now to the actuating lever 2, as discussed above, the actuation of the actuating lever 1, via its actuation block 20, releases the latch 20a, thereby allowing the actuating lever 2 to be actuated. The actuation of the actuating lever 2 causes the push pin 2022 to be released so as to press on a sealing membrane of a fluid reservoir containing a processing fluid, as discussed in more detail below. More specifically, as shown in FIG. 5A, the actuating lever 2 includes a latch 2026 in the form of a protrusion, which is received within a groove 2022a provided in an upper portion of the push pin 2022 so as to lock the push pin 2022 when the actuating lever 2 is in an undeployed position. When the actuating lever 2 is actuated via pressing the actuation block 20, the latch 2026 is disengaged from the groove 2022a, thereby releasing the push pin 2022. Upon release of the push pin 2022, the biasing element 2024, which is in a compressed state when the actuating lever 2 is in undeployed position, will expand so as to exert a downward force on the push pin 2022, which in turn presses on a sealing membrane of the fluid reservoir, thereby causing the release of the processing fluid stored in the fluid reservoir, as discussed in more detail below.

Figure 5D:
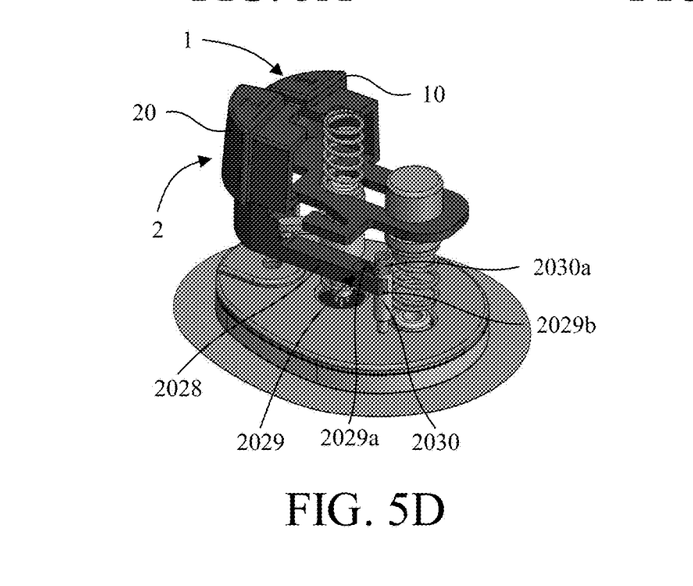
FIG. 5D depicts components of an applicator and a dermal patch wherein a first actuating lever is in a deployed position and a second actuating lever is in an undeployed position in accordance with an exemplary embodiment.
Figure 5E:
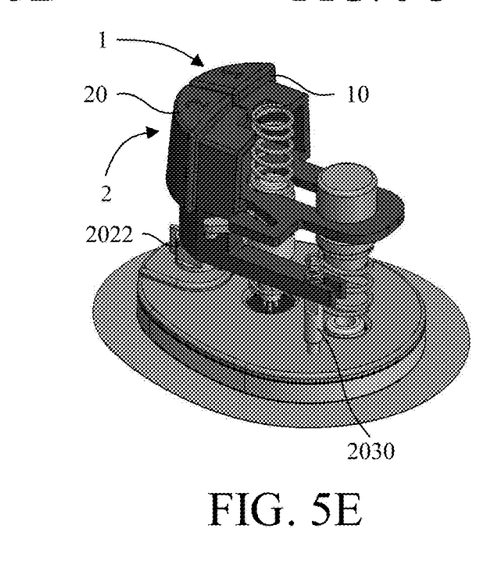
FIG. 5E depicts components of an applicator and a dermal patch wherein a first actuating and a second actuating lever are in a deployed position in accordance with an exemplary embodiment.
Figure 6A:
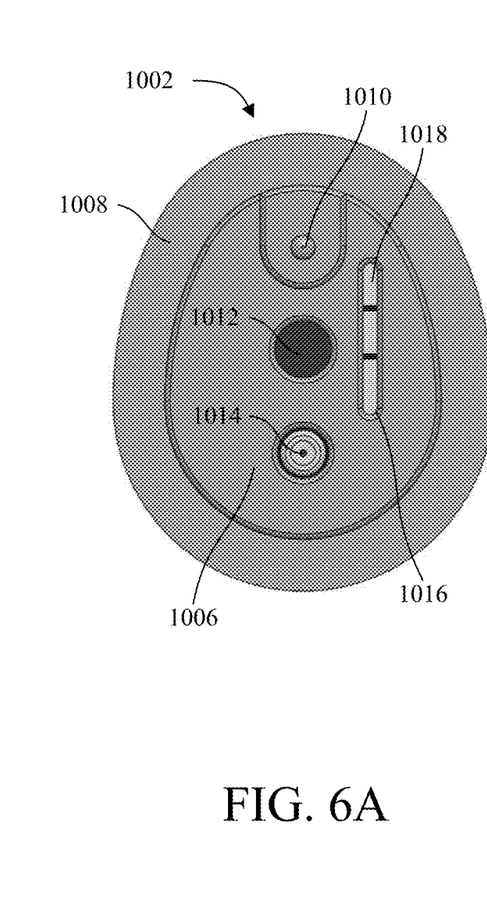
FIG. 6A is a top view of a dermal patch in accordance with an exemplary embodiment.
Figure 6B:
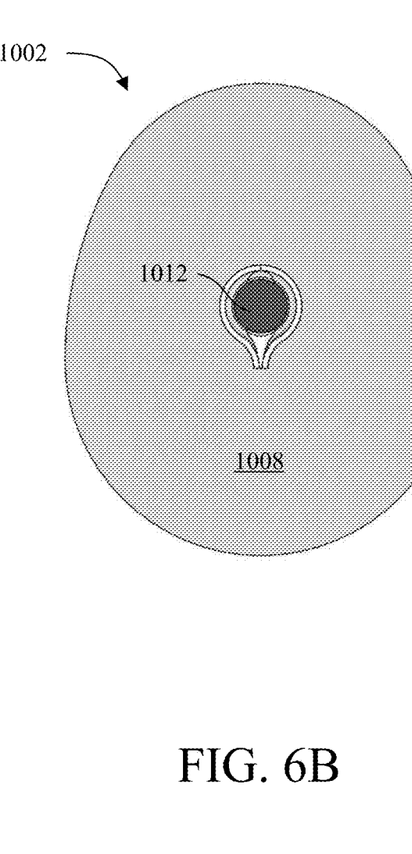
FIG. 6B is a bottom view of a dermal patch in accordance with an exemplary embodiment.
Figure 6C:
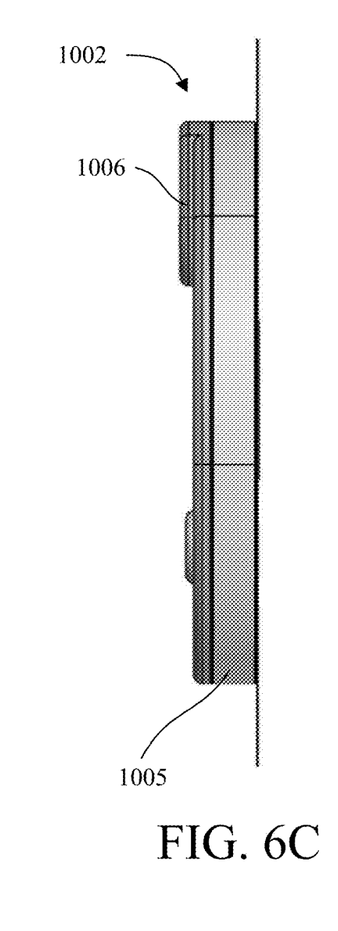
FIG. 6C is a side view of a dermal patch in accordance with an exemplary embodiment.

With particular reference to FIGS. 5D and 5E, the actuating lever 2 includes an actuating arm 2028 having a keyhole-shaped aperture 2029 at its distal end, which is formed of a substantially circular opening 2029a and an elongated channel 2029b having an open tip through which a release pin 2030 can be received in the elongated channel 2029b. A biasing element 2030a is coupled to the upper portion of the release pin 2030. When the actuating lever 2 is in an undeployed position, the release pin 2030 is locked within the elongated channel 2029a and the biasing element 2028a is in a compressed state. As noted above, upon actuation of the actuating lever 2, the actuating arm 2028 moves such that the release pin 2030 is received within the substantially circular opening 2029a of the aperture 2029 and is hence released. As shown in FIG. 5E, upon release of the release pin 2030, the biasing element 2030a expands, thereby exerting a downward force on the release pin that in turn pushes against the dermal patch 1002, thereby releasing the applicator from the dermal patch.

Figure 7:
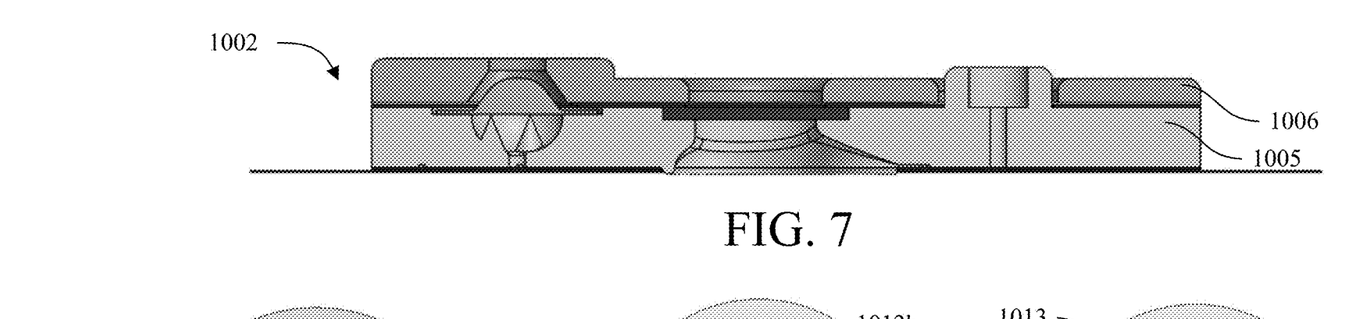
FIG. 7 is a cross sectional view of a dermal patch in accordance with an exemplary embodiment.

Turning now to the dermal patch cartridge 1002, with particular reference to FIG. 1A as well as FIGS. 6A, 6B, 6C, and 6D as well as FIG. 7, the dermal patch cartridge 1002 includes a housing 1005 and a cover 1006. An adhesive layer 1008 in the form of an adhesive strip surrounds the housing 1005 and allows attaching the dermal patch cartridge 1002 to a subject's skin.

The dermal patch cartridge 1002 includes a fluid reservoir 1010, which is herein referred to also as a buffer pack, in which a processing fluid (not visible in the figure) is stored. In addition, in this embodiment, the dermal patch cartridge 1002 includes a septum 1012 formed of a polymeric material, such as polyisoprene, through which the needles 2010 incorporated in the applicator can penetrate, once deployed, to puncture the subject's skin. The dermal patch cartridge 1002 further includes a vacuum luer slip female connector 1014 for connecting the dermal patch cartridge 1002, and more specifically internal fluidic channels of the dermal patch as discussed in more detail below, to the vacuum channel 2012 of the applicator.

In this embodiment, the dermal patch cartridge 1002 includes a sample collection chamber 1016 in which a detector 1018 in the form of a lateral flow strip is positioned. Although in this embodiment the detector 1018 incorporated in the dermal patch cartridge 1002 is a lateral flow strip detection element, in other embodiments other types of detectors can be employed, such as those discussed herein.

When the processing fluid and the physiological sample enter the sample collection chamber 1016, the processing fluid mixes and interacts with the physiological sample to form a processed physiological sample. The detector 1018 may then detect a target analyte within the processed physiological sample. In some embodiments, the detector 1018 may detect a target analyte when the target analyte is equal to or greater than a threshold (e.g., a limit-of detection (LOD)). In other embodiments, the detector may be calibrated to determine a quantitative level of the target analyte (e.g., the concentration of the target analyte in the collected sample).

The detector 1018 may be a variety of different detectors capable of detecting a target analyte (e.g., a graphene-based detector, a chemical detector, a lateral flow detector, a DNA sequencing detector, an RNA sequencing detector, etc.). Furthermore, the detector 1018 may be a passive detector or an active detector and may provide chromatographic or "photo-visual," or digital readouts (e.g., a colorimetric detector, an immunoassay detector including lateral flow detectors, isothermal amplification detection systems, etc.). In some embodiments in which a colorimetric detector is employed, at least a portion of the dermal patch may include a transparent portion to allow the visualization of the detector 1018.

Other suitable means for interrogating a sample may also be employed. By way of example, in some cases, the interrogation of a processed physiological sample may be achieved without the need for direct contact between a detector 1018 and the sample (e.g., optical techniques, such as fluorescent and/or Raman techniques).

In some embodiments, the dermal patch 1002 may include circuitry 1021 that is in communication with the detector 1018 of the dermal patch 1002 and receives one or more signals (e.g., detection signals) generated by the detector 1018. The circuitry 1021 may be configured to process the signals to determine the presence of a target analyte in the processed physiological sample and optionally quantify the level of the target analyte, when present in the processed physiological sample. In addition or instead, the signals generated by the detector 1018 may be processed the circuitry 1021 or an external device to quantify the level of the target analyte detected in the sample. By way of example, such quantification may be implemented using previously-generated calibration data in a manner known in the art as informed by the present teachings. In these embodiments, the circuitry The circuitry 1021 may be implemented using the techniques known in the art. By way of example, the circuitry may include at least one memory module for storing the signals generated by the detector 1018. The circuitry 1021 may be configured to process the stored signals, e.g., detection signals, generated by different types of detector 1018. The circuitry 1021 may also include a communication module to allow communication between the circuitry 1021 and an external electronic device. Such an external electronic device may be a mobile electronic device. By way of example, in some embodiments, a variety of wireless communication protocols may be used for transmitting data from the circuitry to the external electronic device. Some examples of such wireless communication protocols may include Bluetooth, Wi-Fi, and BTLE protocol for establishing a communication link between said patch and said electronic device.

The circuitry 1021 may be implemented on a printed circuit board (PCB), that is in communication with the detector 1018. The connection between the circuitry 1021 and the detector 1018 may be established via any of a wired or wireless protocol. In some embodiments, the circuitry 1021 and/or the detector 1018 can be supplied with power via an on-board power supply, e.g., a battery, incorporated, e.g., on the circuitry. Alternatively, in some implementations, the circuitry and/or the detector can be provided with power via an external device, e.g., a wearable device. Such transfer of power from an external device may be achieved using techniques known in the art, such as inductive coupling between two elements (e.g., two coils) provided in the dermal patch and the external device.

The circuitry 1021 may include an application-specific integrated circuit (ASIC) that is configured for processing the signal data generated by the detector 1018. The circuitry 1021 can further include one or more memory modules for storing, for example, instructions for processing the data generated by the detector 1018.

In other embodiments, the applicator 2000 may include the circuitry 1021. In these embodiments, the applicator 2000 may include a power supply that provides power to the detector 1018.

Figure 8A:
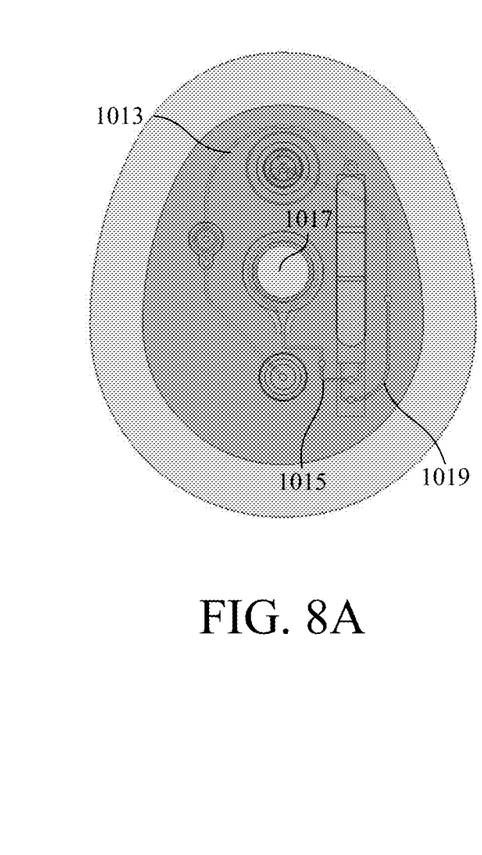
FIG. 8A is a schematic view of dermal patch in accordance with an exemplary embodiment.
Figure 8B:
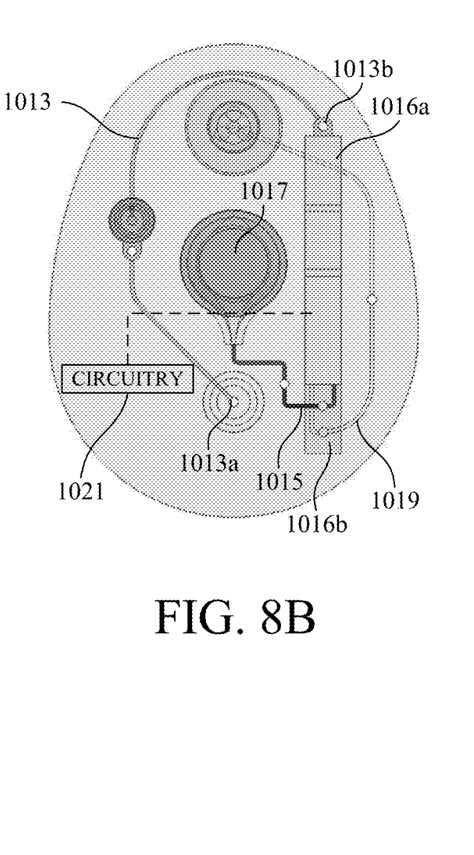
FIG. 8B is another schematic view of dermal patch in accordance with an exemplary embodiment.

While FIG. 8B depicts the dermal patch 1002 as including the circuitry 1021, in some embodiments the circuitry 1021 may be omitted. In these embodiments, the detector 1018 may detect the target analyte without any circuitry 1021 needed (e.g., a lateral flow assay).

In some embodiments, a target analyte may be a pathogen, e.g., a virus or a bacterium. In some embodiments, the detector 1018 can be configured to detect such a pathogen via the detection of a protein or a genetic material thereof, e.g., segments of its DNA and/or RNA. In other embodiments, the detector 1018 may be a lateral flow detector that can be employed to detect a hormone. In other embodiments, the target analyte may be a biomarker, e.g., a biomarker that may be indicative of a disease condition, e.g., organ damage. In some embodiments, the biomarker may be indicative of a traumatic brain injury (TBI), including a mild traumatic brain injury. Some example of such a biomarker include, without limitation, any of myelin basic protein (MBP), ubiquitin carboxyl-terminal hydrolase isoenzyme L1 (UCHL-1), neuron-specific enolase (NSE), glial fibrillary acidic protein (GFAP), and S100-B.

In other embodiments, the dermal patch 1002 may be configured for the detection of other biomarkers, such as troponin, brain natriuretic peptide (BnP), and HbA 1C. Other examples include, but are not limited to, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, HbA1C.

Further, in some embodiments, the detector 1018 may be configured to detect one or more biomarkers for diagnosis of brain damage, such as traumatic brain injury (TBI). Some examples of such biomarkers include, but are not limited to, myelin basic protein (MBP), ubiquitin carboxyl-terminal hydrolase isoenzyme L1 (UCHL-1), neuron-specific enolase (NSE), glial fibrillary acidic protein (GFAP), and S100-B.

By way of example, the detector 1018 may be configured to measure levels of the protein biomarkers UCHL-1 and GFAP, which are released from the brain into blood within 12 hours of head injury. The levels of these two proteins measured by the detector 1018 according to the present disclosure after a mild TBI can help identify those patients that may have intracranial lesions.

In one embodiment a target analyte may be detected the detector 1018 when the detector 1018 is a graphene-based detector that includes a graphene layer that is functionalized with a moiety (e.g., an antibody, an aptamer, an oligonucleotide, etc.) that exhibits specific binding to that target analyte (e.g., a protein, a DNA segment) such that upon binding of the target analyte to that moiety an electrical property of the underlying graphene layer changes, thus indicating the presence of the target analyte in the sample. Some examples of suitable graphene-based detectors are disclosed in U.S. Pat. Nos. 10,782,285, 10,401,352, 9,664,674, as well as published U.S. Patent Applications Nos. 100200011860, and 100210102937, each of which is herein incorporated by reference in their entirety.

By way of example, the detection of a target analyte may be achieved by using a graphene-based detector and/or an electrochemical detector that is functionalized with a probe, such as an antibody and/or aptamer, which exhibits specific binding to that target analyte, though other sensing technologies may also be utilized.

In another embodiment, the detector 1018 may be an electrochemical detector that can function in a faradaic or non-faradaic mode to detect a target analyte of interest. For example, such an electrochemical detector may include a working electrode, a reference electrode and a counter electrodes. By way of example, in some embodiments, the reference electrode may be functionalized with a moiety that exhibits specific binding to a target analyte such that upon binding of that target analyte, when present in the sample, to the moiety, a change in the current through the circuit may be detected.

In some embodiments, at least one serum-separation element is associated with the detector 1018 for receiving blood and separating a serum/plasma component of the blood for introduction into said at least one of the sensing units.

The serum-separating element may include a fibrous element that is configured to capture one or more cellular components of the blood so as to separate a plasma/serum component of the blood for analysis. For example, in such embodiments, the serum component can be introduced in a respective sensing unit for analysis, e.g., for detection and optionally quantification of one or more biomarkers and/or other analytes. In some embodiments, the serum-separating element is a nitrocellulose strip. The use of such a fibrous element, and in particular a nitrocellulose strip, can allow sufficient fractionation of the blood to enhance significantly the sensitivity/specificity of detection of analytes (e.g., biomarkers) in the separated serum, especially using a graphene-based sensor. In other words, although the use of a nitrocellulose strip in a patch according to some embodiments may not result in fractionation of the whole blood sample with the same degree of separation quality that is achievable via traditional fractionation methods, such as differential centrifugation; nonetheless, the applicant has discovered that the use of such a nitrocellulose strip in embodiments of the dermal patch can significantly enhance the sensitivity/specificity for the detection of a variety of analytes (e.g., biomarkers) using a variety of detectors, such as graphene-based detectors, relative to the use of a whole blood sample for such detection. In some embodiments, wherein the detector 1018 is a graphene sensor, the nitrocellulose strip may be coupled to the detector 1018 and the detector 1018 may detect the target analyte via the nitrocellulose strip.

Furthermore, the serum-separation element may include at least one fibrous membrane configured to capture at least a portion of one or more cellular components of the received blood, thereby separating a serum (or a plasma) component of the blood.

In some embodiments, the separated plasma or the serum component can still include some cellular elements. Even without having a level of fractionation that is achieved via traditional methods, such as differential centrifugation, the separated serum component can be utilized to achieve an enhanced detection sensitivity/specificity relative to using whole blood for detecting, and optionally quantifying, a variety of target analytes in a drawn blood sample. Some examples of such target analytes may include, without limitation, a biomarker, such as troponin, brain natriuretic peptide (BnP), or other biomarkers including those disclosed herein.

The separated serum component may include any of a plurality of red blood cells and/or a plurality of white blood cells and/or platelets. However, the concentration of such cellular components in the separated serum component can be less than that in the whole blood by a factor in a range of about 2 to about 1000, though lower concentrations can also be achieved.

In use, the dermal patch cartridge 1002 can be attached to a subject's skin via the adhesive layer 1008. In some embodiments, a removable liner (not shown in the figure) covering the adhesive surface of the adhesive patch 1008 can be removed to expose the adhesive surface for attachment onto the subject's skin.

The applicator 2000 can then be coupled to the dermal patch cartridge 1002 for activating the dermal patch cartridge 1002. After coupling the applicator 2000 to the dermal patch cartridge 1002, the actuating lever 1 can be activated to deploy the needles 2010 via penetration through the septum 1012 to puncture the subject's skin in a manner discussed above.

As noted above, the actuation of the actuating lever 1 also causes the creation of a vacuum in the vacuum chamber 2012.

Figure 8C:
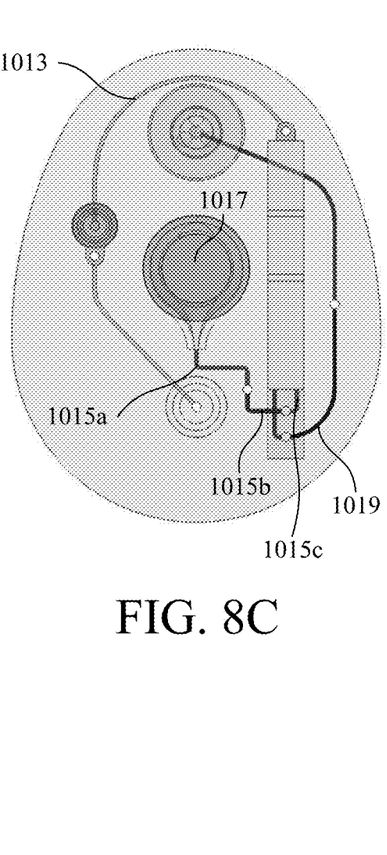
FIG. 8C is yet another schematic view of dermal patch in accordance with an exemplary embodiment.

With reference to FIGS. 8A, 8B, and 8C, upon activation of the actuating lever 1, the vacuum created in the vacuum chamber 2012 generates a vacuum in a fluidic channel 1013 that extends from a proximal end 1013a that is in fluid communication with the vacuum chamber 2012 to a distal end 1013b that is in fluid communication with one end 1016a of the sample collection chamber 1016 in which the lateral strip 1018 is disposed to apply a vacuum thereto.

The dermal patch cartridge 1002 further includes a fluidic channel 1015 that extends from a blood receiving receptacle 1017 to another end 1016b of the sample collection chamber 1016 in which the lateral flow strip is positioned. In this embodiment a via in the form a vertical fluidic channel connects a first portion 1015a of the fluidic channel 1015, which is in proximity of an upper surface of the dermal patch, to a second portion 1015b of the fluidic channel 1015, which is in proximity of a lower surface of the dermal patch, to guide the drawn blood sample to a level above the lateral flow strip 1018, which can then be released onto the lateral flow strip 1018 through a third portion 1015c of the fluidic channel 1015, which receive the blood from the second portions 1015b of the fluidic channel 1015 through a via.

The vacuum applied to the sample collection chamber 1016 in which the lateral flow strip is positioned facilitates the flow of the drawn blood through the fluidic channel 1015 onto the detector 1018.

While the above describes the sample collection chamber 1016 as including a detector 1018, in other embodiments, the detector 1018 may be omitted. In these embodiments, the sample collection chamber 1016 may be configured to store the processed physiological sample so that the processed physiological sample may be analyzed at a later time as previously described herein. In some such embodiments, a storage element, e.g., in the form of a cellulose matrix, may be in communication with the sample collection chamber to collect at least a portion of the drawn physiological sample for analysis.

In another embodiment, the dermal patch 1002 may include a second sample collection chamber 1016. In this embodiment, the fluidic channel 1015 branches such that the fluidic channel 1015 carries the physiological sample to both sample collection chambers 1016 and the fluidic channel 1019 branches to carry processing fluid to both sample collection chambers 1016. The fluidic channel 1019 carries the processing fluid from the fluid reservoir to the sample collection chamber 1016 and/or the detector 1018.

With particular reference to FIGS. 1A, 1B, and 3A, a window provided in the applicator can allow visual inspection of the lateral flow strip. Such visual inspection can be used to observe the result of the test provided by the lateral flow strip. The window can be also be utilized during blood collection to observe the amount of blood accumulated over in the sample collection chamber 1016 in which the lateral flow strip is positioned so as to allow a user to activate the actuating lever 2 only when sufficient blood is present in the well.

The dermal patch cartridge and the applicator can be fabricated using a variety of different materials. For example, polymeric materials, such as PDMS (polydimethyl siloxane) can be used for fabrication various components, e.g., the housings of the dermal patch cartridge and/or the applicator.

In some embodiments, rather than utilizing an applicator, a dermal patch according to the present teachings can be activated by a user using an implement, e.g., a lancet enclosed in a trocar. By way of example, with reference to FIG. 9, a dermal patch 1002 according to the present teachings can be coupled to a patient's upper arm, e.g., via an elastic band having a hook-and-loop fastener that can apply a moderate pressure to the subject's arm. A lancet 902 can be used to penetrate through the septum 1012 of the dermal patch 1002 so as to puncture the skin so as to allow blood to enter the dermal patch under the influence of the pressure applied to the subject's arm. The lancet 902 may include a pressure or a vacuum bulb that a user may push to promote the flow of the physiological sample to the sample collection chamber 902.

Figure 9:
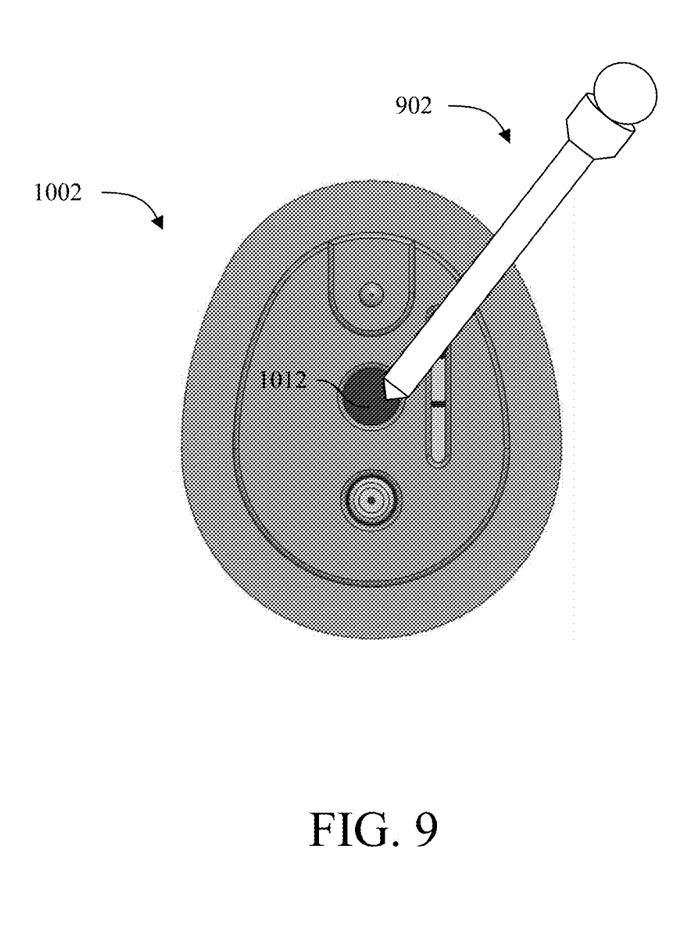
FIG. 9 depicts a lancet and a dermal patch in accordance with an exemplary embodiment.

Subsequently, the same trocar having a lancet can be used to cause the release of the processing fluid (or at least a portion thereof) from the fluid reservoir for mixing with the drawn blood sample. For example, the lancet may retracted into the trocar and the tip of the trocar can be pressure on a flexible membrane sealing the fluid reservoir to cause the fluid to be released from the fluid reservoir, e.g., in a manner discussed above in connection with the applicator.

In other embodiments, the needles 2010, after drawing the physiological sample, may apply positive pressure to push the drawn physiological sample to the sample collection chamber 1016. In these embodiments, the syringe 2014 and the fluidic channel 1013 may be omitted.

What is claimed is:

1. A system comprising:
   an applicator including:
   a needle configured to puncture a subject's skin to draw a physiological sample;
   a first actuating lever configured to move from an undeployed position to a deployed position, and
   a second actuating lever configured to move from an undeployed position to a deployed position,
   a latch configured to maintain the second actuating lever in a locked position so as to inhibit movement thereof when the first actuating lever is in the undeployed position and configured to be released upon actuation of the first actuating lever so as to allow actuation of the second actuating lever and;
   a dermal patch configured for coupling to the applicator and including:
   a fluid reservoir configured to store a processing fluid,
   a sample collection chamber configured to receive the processing fluid and the physiological sample,
   wherein the applicator is configured to:
   cause the needle to puncture the subject's skin to draw the physiological sample when the first actuating lever is moved from the undeployed lever position to the deployed lever position and cause the processing fluid to be released from the fluid reservoir when the second actuating lever is moved from the undeployed position to the deployed position.

2. The system of claim 1, wherein the dermal patch is removably coupled to the applicator.

3. The system of claim 1, wherein the dermal patch is integrally coupled to the applicator.

4. The system of claim 1, wherein the physiological sample includes blood.

5. The system of claim 1, wherein the processing fluid includes an anti-coagulant.

6. The system of claim 5, wherein the processing fluid includes heparin or a protease inhibitor.

7. The system of claim 1, further comprising:
an adhesive layer coupled to the dermal patch, wherein the adhesive layer is configured to attach to skin of the subject.

8. The system of claim 1, wherein the latch is coupled to the second actuating lever, is maintained within a recess of the first actuating lever, and is configured to move to a released position within the recess when the first actuating lever is moved to the deployed position.

9. The system of claim 1, wherein the applicator further comprises:
a syringe configured to create a vacuum within the dermal patch when the first actuating lever is moved from the deployed position to the undeployed position, wherein the vacuum draws the physiological sample and the released processing fluid to flow to the sample collection chamber.

10. A system comprising:
an applicator including:
a needle configured to puncture a subject's skin to draw a physiological sample;
a first actuating lever configured to move from an undeployed position to a deployed position, and
a second actuating lever configured to move from an undeployed position to a deployed position,
a latch configured to maintain the second actuating lever in a locked position so as to inhibit movement thereof when the first actuating lever is in the undeployed position and configured to be released upon actuation of the first actuating lever so as to allow actuation of the second actuating lever and;
a dermal patch configured for coupling to the applicator and including:
a fluid reservoir configured to store a processing fluid,
a detector configured to detect a target analyte in a processed physiological sample resulting from processing the physiological sample by the processing fluid, wherein the applicator is configured to:
cause the needle to puncture the subject's skin to draw the physiological sample when the first actuating lever is moved from the undeployed lever position to the deployed lever position and cause the processing fluid to release from the fluid reservoir when the second actuating lever is moved from the undeployed position to the deployed position.

11. The system of claim 10, wherein the detector is configured to detect the target analyte when the target analyte is present in the processed physiological sample at a concentration level equal to or greater than a threshold amount.

12. The system of claim 10, wherein the processing fluid includes a reagent for isothermal amplification of the target analyte.

13. The system of claim 10, wherein the target analyte includes a biomarker.

14. The system of claim 13, wherein the biomarker is troponin, brain natriuretic peptide (BnP), myelin basic protein (MBP), ubiquitin carboxyl-terminal hydrolase isoenzyme L1 (UCHL-1), neuron-specific enolase (NSE), glial fibrillary acidic protein (GFAP), S100-B, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, or HbA1C.

15. The system of claim 10, wherein the detector is an immunoassay detector, an isothermal amplification detection system, a graphene-based detector, an electrochemical detector, and chemical detector.

16. The system of claim 10, wherein the second actuating lever is in locked state when the first actuating lever is in the undeployed position.

17. The system of claim 16, wherein the applicator further comprises:
wherein the latch is coupled to the second actuating lever, is maintained within a recess of the first actuating lever and is configured to move to a released position within the recess when the first actuating lever is moved to the deployed position and wherein the latch is configured to allow actuating of the second actuating lever when in the released position.

18. The system of claim 10, wherein the applicator further comprises:
a syringe configured to create a vacuum within the dermal patch when the first actuating lever is moved from the deployed position to the undeployed position, wherein the vacuum draws the physiological sample and the released processing fluid to flow to the sample collection chamber.

19. The system of claim 10, wherein the applicator is removably coupled to the dermal patch.

* * * * *